(12) United States Patent
Igarashi

(10) Patent No.: US 11,782,659 B2
(45) Date of Patent: Oct. 10, 2023

(54) INFORMATION PROCESSING APPARATUS, PRINTING APPARATUS, AND METHOD OF DETERMINING PRINT MEDIA TYPE

(71) Applicant: CANON KABUSHIKI KAISHA, Tokyo (JP)

(72) Inventor: Yuki Igarashi, Tokyo (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 16/748,699

(22) Filed: Jan. 21, 2020

(65) Prior Publication Data
US 2020/0249889 A1 Aug. 6, 2020

(30) Foreign Application Priority Data

Jan. 31, 2019 (JP) ................................. 2019-016168

(51) Int. Cl.
G06F 3/12 (2006.01)

(52) U.S. Cl.
CPC .......... *G06F 3/1254* (2013.01); *G06F 3/1204* (2013.01)

(58) Field of Classification Search
None
See application file for complete search history.

(56) References Cited

U.S. PATENT DOCUMENTS

| | | | | |
|---|---|---|---|---|
| 7,808,672 B2* | 10/2010 | Wu | ....................... | G06F 3/1205 358/1.6 |
| 11,025,791 B2* | 6/2021 | Igarashi | ............. | H04N 1/00427 |
| 11,161,357 B2* | 11/2021 | Kasamatsu | ............ | B41J 11/009 |
| 11,639,068 B2* | 5/2023 | Eiyama | ................. | G06F 3/1204 347/19 |
| 2004/0246290 A1* | 12/2004 | Hayashi | ................. | B41J 13/103 347/19 |
| 2005/0030334 A1 | 2/2005 | Kai | | |
| 2007/0002349 A1* | 1/2007 | Hwang | ................. | G06F 3/1204 358/1.13 |

(Continued)

FOREIGN PATENT DOCUMENTS

| | | |
|---|---|---|
| CN | 1319303 A | 10/2001 |
| CN | 1581056 A | 2/2005 |

(Continued)

*Primary Examiner* — Barbara D Reinier
(74) *Attorney, Agent, or Firm* — Canon U.S.A., Inc. I.P. Division

(57) ABSTRACT

An information processing apparatus includes an acquisition unit configured to acquire a measurement result obtained by a measurement unit that measures a characteristic of a print medium to be used in a printing apparatus, a notification control unit configured to cause a notification unit to provide notification of information indicating a print media type, and a storage unit configured to store information on a predetermined characteristic of each of a plurality of print media types, wherein, based on the measurement result acquired by the acquisition unit and usage history information indicating print media types used in the printing apparatus, the notification control unit causes the notification unit to provide notification of information indicating a print media type for which information on the predetermined characteristic stored in the storage unit corresponds to a characteristic indicated in the measurement result and which has a usage history indicated in the usage history information.

27 Claims, 12 Drawing Sheets

(56) References Cited

U.S. PATENT DOCUMENTS

| | | |
|---|---|---|
| 2011/0135322 A1 | 6/2011 | Masuyama |
| 2017/0068494 A1 | 3/2017 | Fukuda |
| 2018/0253049 A1* | 9/2018 | Sakakibara ........ G03G 15/6511 |

FOREIGN PATENT DOCUMENTS

| CN | 1615223 A | 5/2005 | |
|---|---|---|---|
| CN | 102638640 A | 8/2012 | |
| CN | 104822003 A | 8/2015 | |
| CN | 108535990 A | 9/2018 | |
| EP | 2487893 A | 8/2012 | |
| EP | 2487893 A1 * | 8/2012 | ........... H04N 1/6033 |
| JP | 2004-122766 * | 4/2004 | |
| JP | 2005038277 A | 2/2005 | |
| JP | 2005-070877 * | 3/2005 | |
| JP | 2012093601 A | 5/2012 | |
| JP | 2016-215591 A | 12/2016 | |

\* cited by examiner

FIG.6A
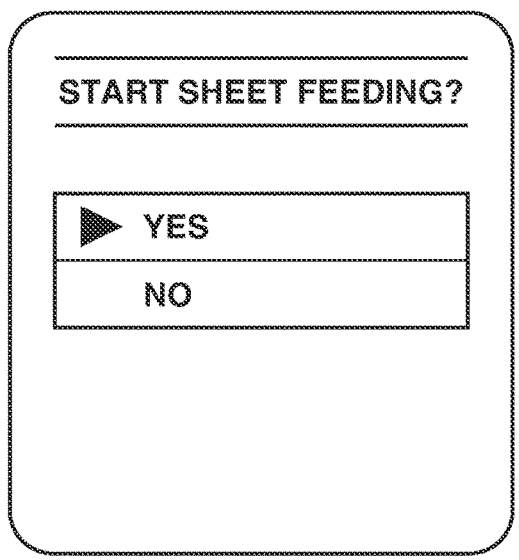
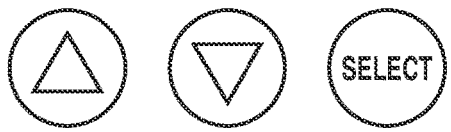
FIG.6B
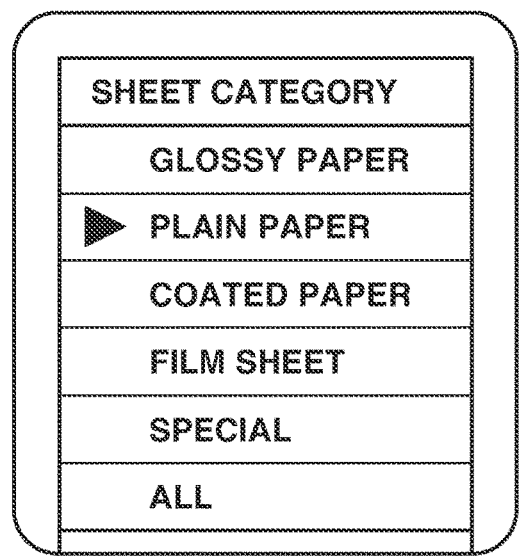
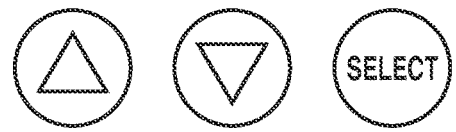
FIG.6C
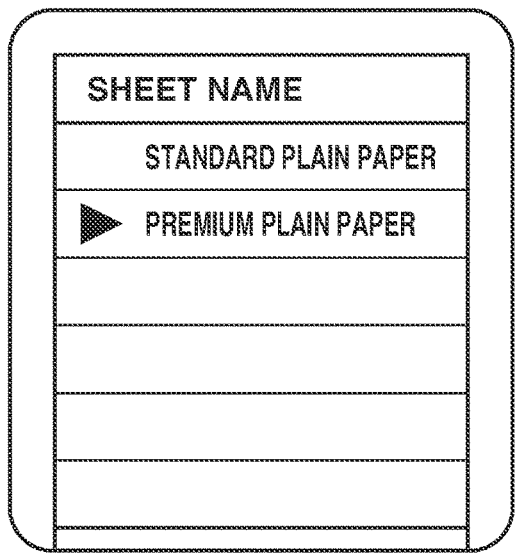
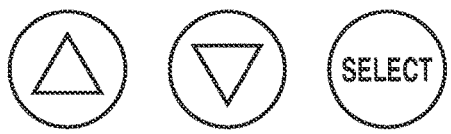
FIG.6D
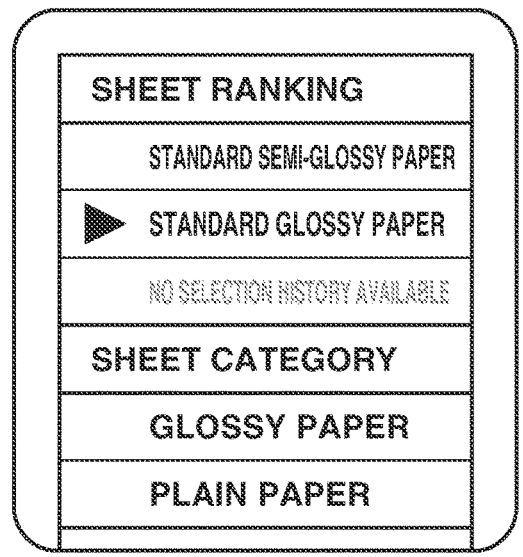
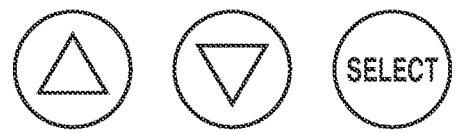

FIG.7A

|  | DIFFUSED REFLECTION VALUE | SPECULAR REFLECTION VALUE | PAPER THICKNESS [μm] |
|---|---|---|---|
| STANDARD GLOSSY PAPER | 100 | 100 | 180 |
| STANDARD SEMI-GLOSSY PAPER | 99 | 95 | 180 |
| PREMIUM GLOSSY PAPER | 105 | 115 | 210 |
| THICK GLOSSY PAPER | 100 | 100 | 270 |
| STANDARD PLAIN PAPER | 90 | 75 | 95 |
| PREMIUM PLAIN PAPER | 95 | 83 | 110 |

FIG.7B

|  | DIFFUSED REFLECTION VALUE | SPECULAR REFLECTION VALUE | PAPER THICKNESS [μm] |
|---|---|---|---|
| SENSOR READING VALUE 1 | 103 | 98 | 190 |
| EXTRACTION RANGE | 98 – 108 | 95 – 103 | 140 – 230 |

|  | DIFFUSED REFLECTION VALUE | SPECULAR REFLECTION VALUE | PAPER THICKNESS [μm] |
|---|---|---|---|
| STANDARD GLOSSY PAPER | (100) | (100) | (180) |
| STANDARD SEMI-GLOSSY PAPER | (99) | (95) | (180) |
| PREMIUM GLOSSY PAPER | (105) | 115 | (210) |
| THICK GLOSSY PAPER | (100) | (100) | 270 |
| STANDARD PLAIN PAPER | (90) | 75 | 95 |
| PREMIUM PLAIN PAPER | (95) | 83 | 110 |

FIG.7C

|  | DIFFUSED REFLECTION VALUE | SPECULAR REFLECTION VALUE | PAPER THICKNESS [μm] |
|---|---|---|---|
| SENSOR READING VALUE 2 | 88 | 150 | 90 |
| EXTRACTION RANGE | 83 – 93 | 145 – 155 | 40 – 130 |

|  | DIFFUSED REFLECTION VALUE | SPECULAR REFLECTION VALUE | PAPER THICKNESS [μm] |
|---|---|---|---|
| STANDARD GLOSSY PAPER | 100 | 100 | 180 |
| STANDARD SEMI-GLOSSY PAPER | 99 | 95 | 180 |
| PREMIUM GLOSSY PAPER | 105 | 115 | 210 |
| THICK GLOSSY PAPER | 100 | 100 | 270 |
| STANDARD PLAIN PAPER | (90) | 75 | (95) |
| PREMIUM PLAIN PAPER | 95 | 83 | (110) |

FIG.8A

| ORDER IN HISTORY | |
|---|---|
| 1 | PREMIUM PLAIN PAPER |
| 2 | STANDARD SEMI-GLOSSY PAPER |
| 3 | PREMIUM GLOSSY PAPER |
| 4 | THICK GLOSSY PAPER |
| 5 | STANDARD GLOSSY PAPER |
| 6 | STANDARD PLAIN PAPER |

FIG.8B

| ORDER IN HISTORY | |
|---|---|
| 1 | STANDARD GLOSSY PAPER |
| 2 | PREMIUM PLAIN PAPER |
| 3 | STANDARD SEMI-GLOSSY PAPER |
| 4 | PREMIUM GLOSSY PAPER |
| 5 | THICK GLOSSY PAPER |
| 6 | STANDARD PLAIN PAPER |

FIG.8C

| ORDER IN HISTORY | |
|---|---|
| 1 | PREMIUM PLAIN PAPER |
| 2 | STANDARD SEMI-GLOSSY PAPER |
| 3 | PREMIUM GLOSSY PAPER |
| 4 | |
| 5 | |
| 6 | |

FIG.9A
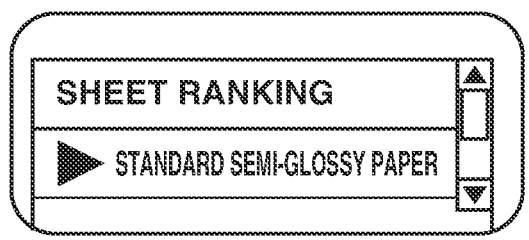
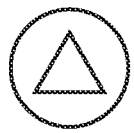 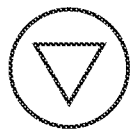 
FIG.9B
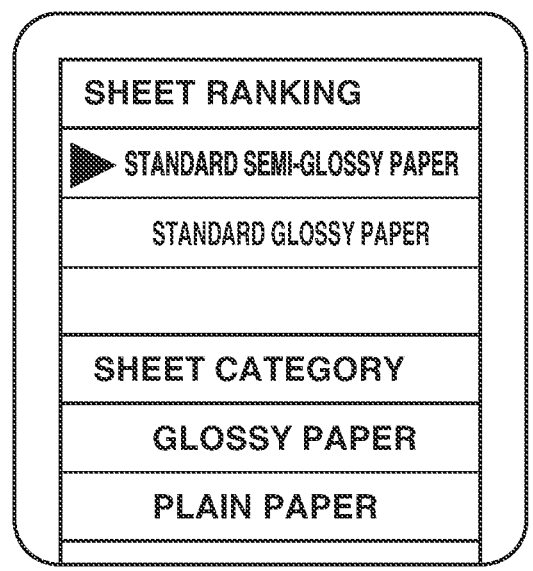
 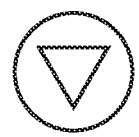 
FIG.9C
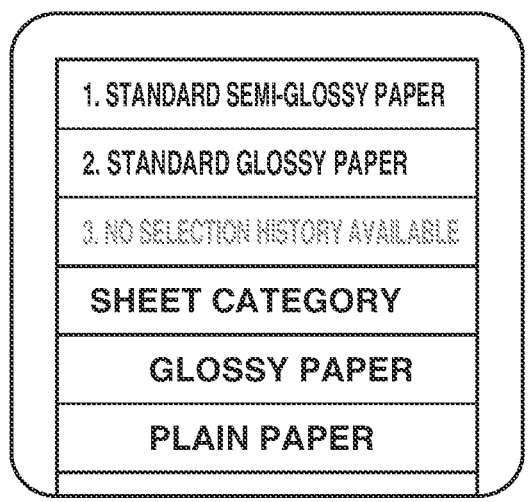
FIG.9D
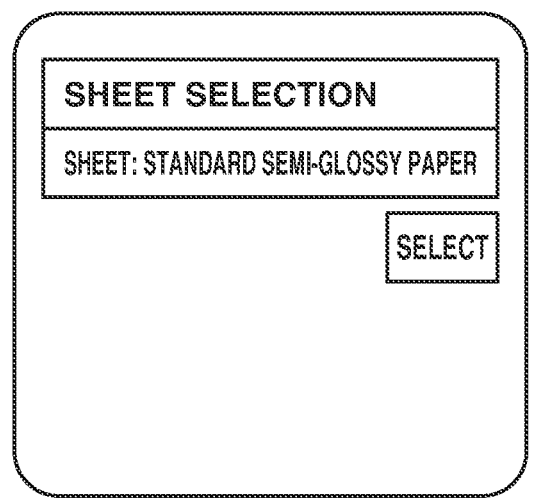

FIG.11
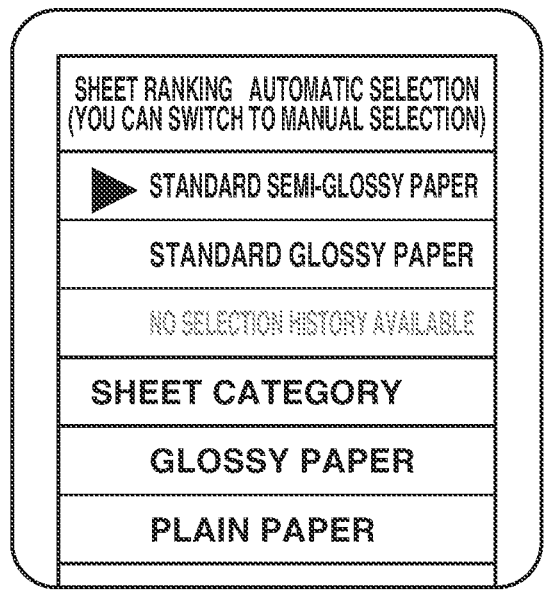
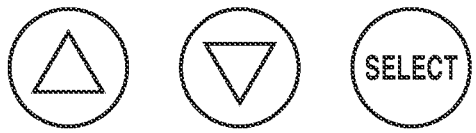

INFORMATION PROCESSING APPARATUS, PRINTING APPARATUS, AND METHOD OF DETERMINING PRINT MEDIA TYPE

BACKGROUND OF THE INVENTION

Field of the Invention

The present invention relates to an information processing apparatus, a printing apparatus, and a method of determining a print media type.

Description of the Related Art

When images having high-definition quality are printed by printing apparatuses, printing is performed using control parameters corresponding to a print media type. In technique discussed in Japanese Patent Application Laid-Open No. 2016-215591, a plurality of characteristic values of a print medium on which printing is to be performed is measured and a print media type is determined to use appropriate control parameters in printing.

SUMMARY OF THE INVENTION

Some print media of different types have characteristic values similar to each other. The technique discussed in Japanese Patent Application Laid-Open No. 2016-215591 therefore sometimes fails to correctly determine a print media type due to measurement errors or the like. The failure can impair user convenience.

The present invention has been made in view of the above described issue and is directed to improvement in determination of a print media type to enhance user convenience.

According to an aspect of the present invention, an information processing apparatus includes an acquisition unit configured to acquire a measurement result obtained by a measurement unit that is configured to measure a characteristic of a print medium to be used in a printing apparatus, a notification control unit configured to cause a notification unit to provide notification of information indicating a print media type, and a storage unit configured to store information on a predetermined characteristic of each of a plurality of print media types, wherein, based on the measurement result acquired by the acquisition unit and usage history information indicating print media types used in the printing apparatus, the notification control unit causes the notification unit to provide notification of information indicating a print media type for which information on the predetermined characteristic stored in the storage unit corresponds to a characteristic indicated in the measurement result and which has a usage history indicated in the usage history information.

Further features of the present invention will become apparent from the following description of exemplary embodiments with reference to the attached drawings.

BRIEF DESCRIPTION OF THE DRAWINGS

FIGS. 6A, 6B, 6C, and 6D are diagrams illustrating display forms of an input/output unit according to the first exemplary embodiment.

FIGS. 7A, 7B, and 7C are diagrams each illustrating a table for the print medium determination according to the first exemplary embodiment.

FIGS. 8A, 8B, and 8C are diagrams each illustrating a table for history information according to the first and exemplary embodiment and a second exemplary embodiment.

FIGS. 9A, 9B, 9C, and 9D are diagrams illustrating other display forms of the input/output unit, FIG. 11 is a diagram illustrating a display form of an input/output unit according to a fourth exemplary embodiment and FIG. 12 is a flowchart illustrating a print medium determination processing according to the fourth exemplary embodiment.

DESCRIPTION OF THE EMBODIMENTS

<Entire Configuration>

Figure 1A:
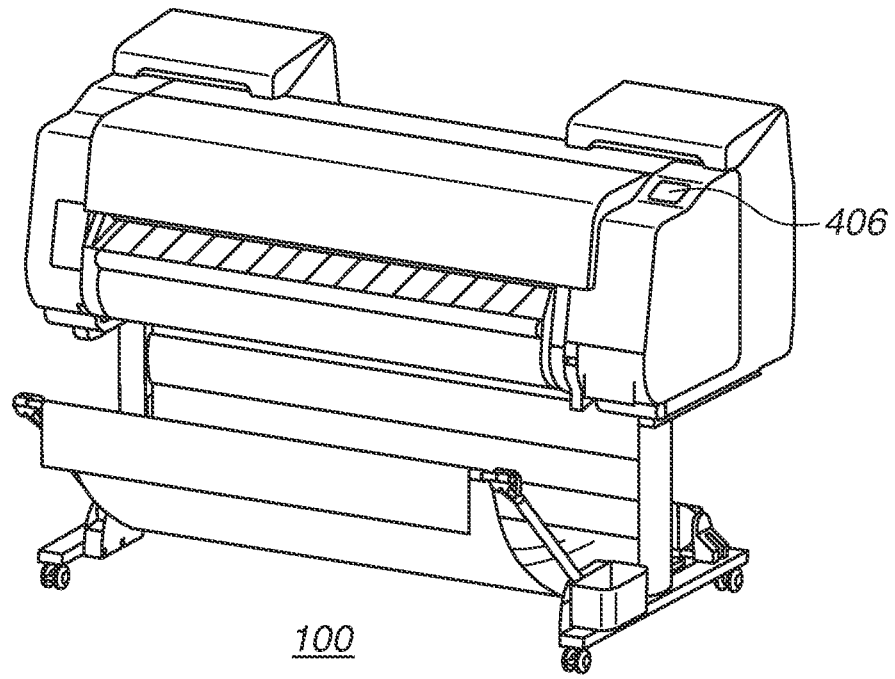
FIGS. 1A and 1B are perspective views each illustrating a configuration of a printing apparatus according to a first exemplary embodiment.
Figure 1B:
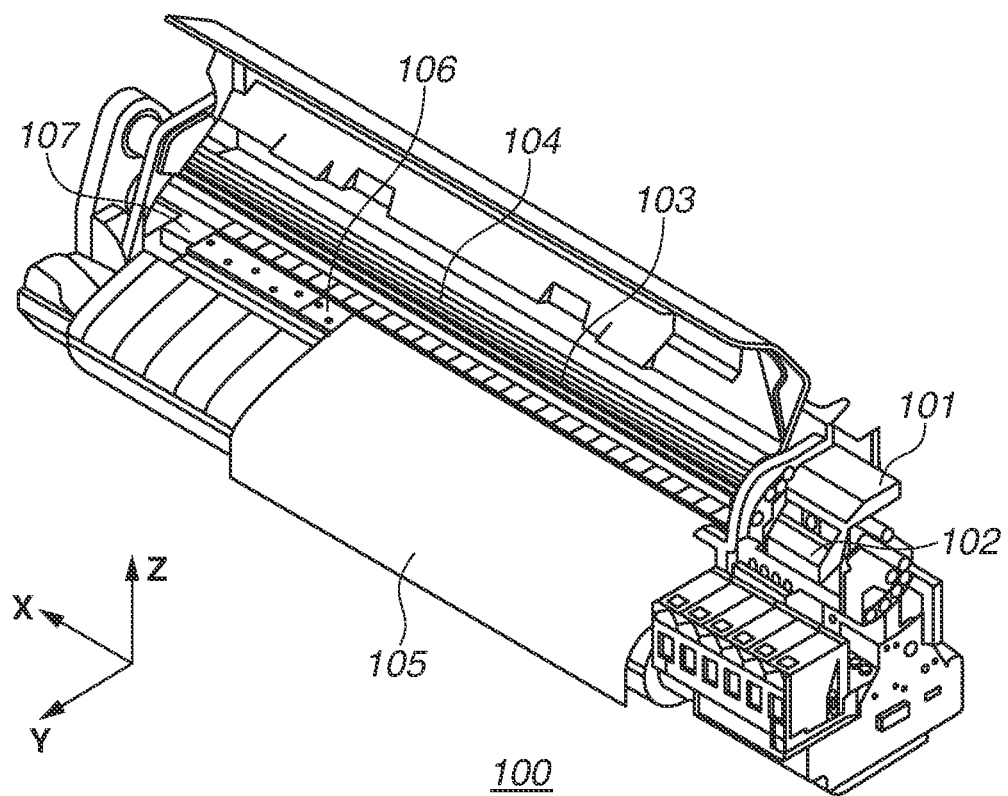

FIGS. 1A and 1B are perspective views illustrating the configuration of a printing apparatus according to a first exemplary embodiment, FIG. 1A illustrates an outer appearance of the entire printing apparatus, FIG. 1B illustrates an internal structure of the printing apparatus with an upper cover opened and with a casing omitted from the illustration. The printing apparatus 100 according to the present exemplary embodiment employs an ink jet printing method and performs printing by discharging ink droplets as a printing agent on a print medium. The print medium is conveyed in a Y direction which is a conveyance direction. Description will be given of an ink jet printing apparatus including what is called a serial print head, in printing using the serial print head, a carriage 101 on which a print head 102 used as printing means is mounted reciprocally moves in an X direction intersecting the Y direction. Alternatively, an ink jet printing apparatus including what is called a line printing head may be used. In the line printing head, a row of nozzles is disposed across a printing width intersecting the print medium conveyance direction. A multifunction peripheral (MFP) may also be used. In the WI), a scanning function, a facsimile function, a transmission function, and the like are combined together with a printing function. In the present exemplary embodiment, the function of the information processing apparatus for print medium determination processing for determining a print medium to be used is installed in the printing apparatus 100. The print medium determination processing is described below.

An input/output unit 406 is disposed on an upper part of the printing apparatus 100. The input/output unit 406 is an operation panel and displays a remaining ink amount and a candidate or candidates of a print media type on a display device, and a user can select a print medium and input settings for printing using keys.

Figure 2:
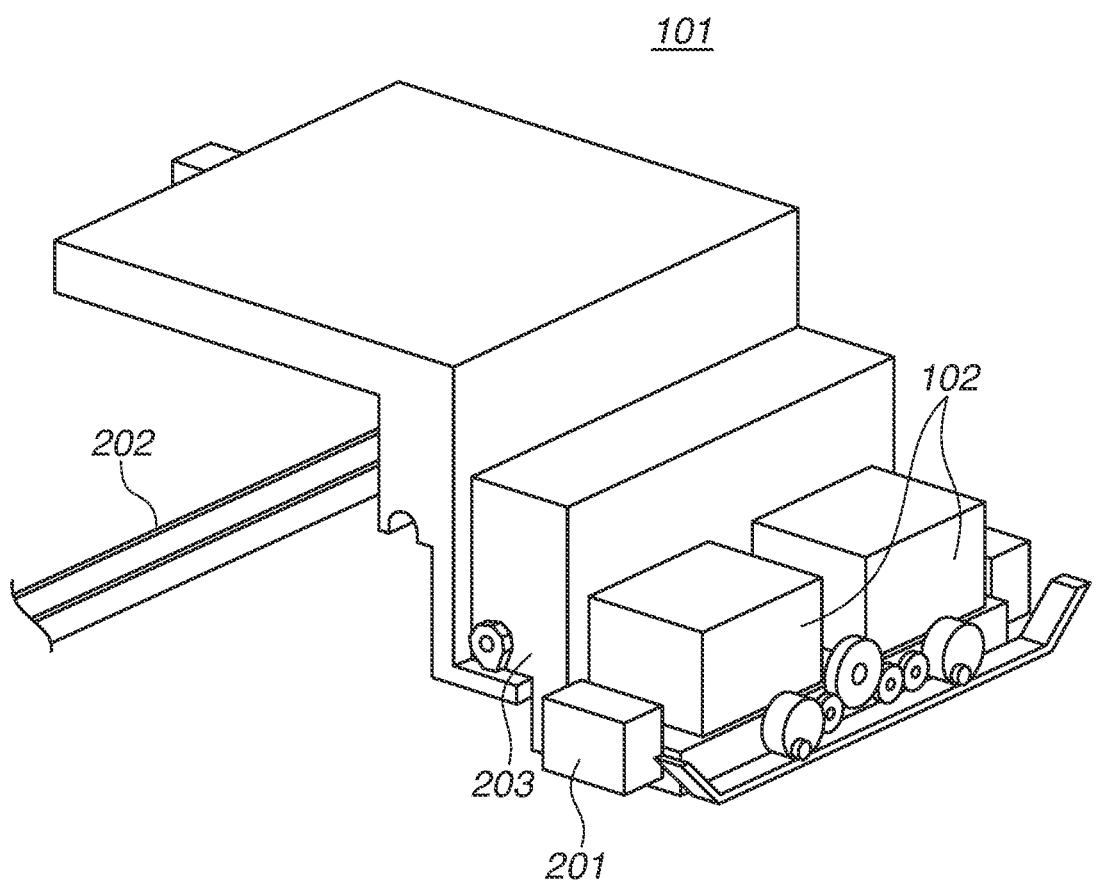
FIG. 2 is a diagram illustrating the configuration of a carriage according to the first exemplary embodiment.

The carriage 101 includes an optical sensor 201 illustrated in FIG. 2 and the print head 102 on which a discharge port surface having discharge ports through which ink is discharged. The carriage 101 can reciprocally move in the X direction (a moving direction of the carriage 101) along a shaft 104 by driving force transmitted from a carriage motor 415 illustrated in FIG. 4 via a conveyance belt 103 used as conveyance means. In the present exemplary embodiment, the printing apparatus 100 can acquire a diffused reflection characteristic value and a specular reflection characteristic value on a surface of the print medium 105 and measure a distance between the carriage 101 and the print medium 105 using the optical sensor 201.

The print medium 105, such as roll paper, is conveyed on a platen 106 in the Y direction by conveyance rollers not illustrated. Ink droplets discharged from the print head 102 while the carriage 101 moves in the X direction on the print medium 105 conveyed on the platen 106 by the conveyance rollers so that printing is performed. When the carriage 101 reaches an edge of a print area on the print medium 105, the conveyance rollers convey the print medium 105 by a predetermined amount to move an area of the print medium 105 on which subsequent scan for printing is performed to a position where the print head 102 can perform printing. An image is printed through repetition of the above operation.

<Carriage Configuration>

FIG. 2 is a diagram illustrating a configuration of the carriage 101. The carriage 101 includes a translator 202 and a head holder 203. The head holder 203 includes print heads 102 and an optical sensor 201 that is a reflective sensor. As illustrated in FIG. 2, the bottom face of the optical sensor 201 is arranged at the same level as or higher than the bottom faces of the print heads 102, <Optical Sensor Configuration>

Figure 3:
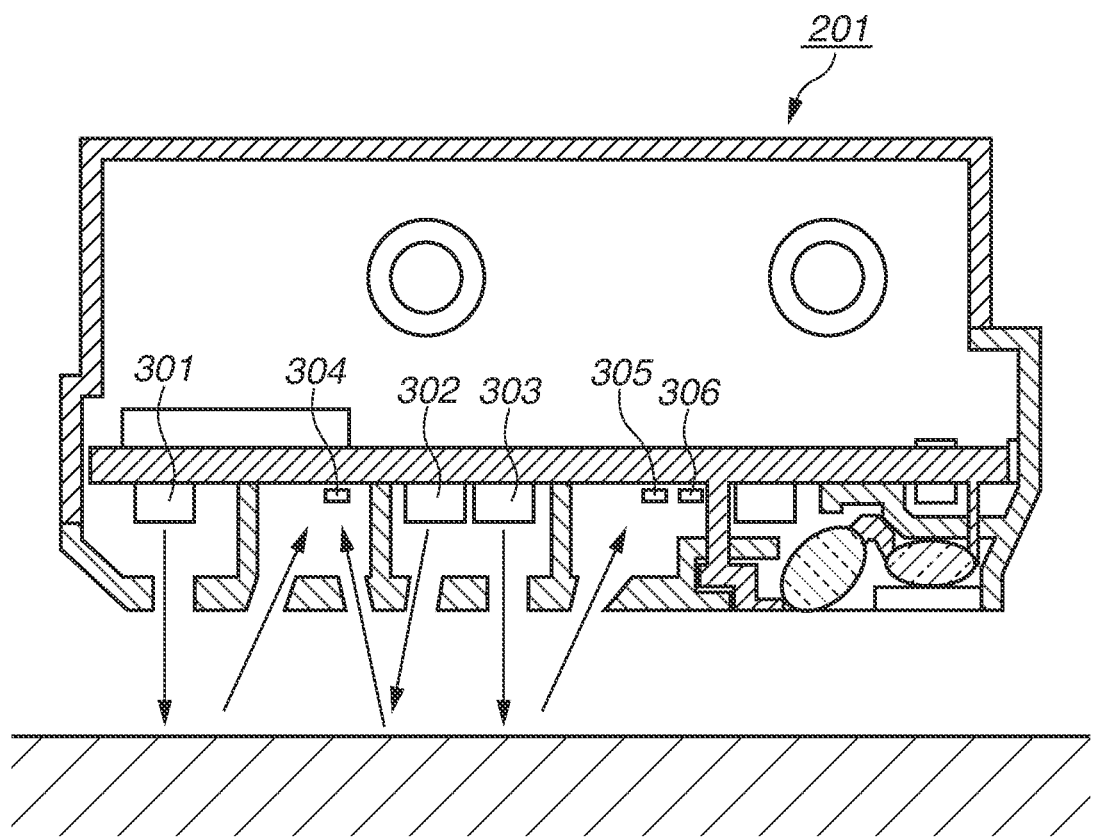
FIG. 3 is a diagram illustrating the configuration of an optical sensor according to the first exemplary embodiment.

FIG. 3 is a sectional schematic view illustrating the configuration of the optical sensor 201. The optical sensor 201 includes a first light-emitting diode (LED) 301, a second LED 302, a third LED 303, a first photodiode 304, a second photodiode 305, and a third photodiode 306 as optical elements. The first LED 301 is a light source having an irradiation angle of the normal line (90°) with respect to a surface (measured surface) of the print medium 105. The first photodiode 304 receives light projected from the first LED 301 and reflected from the print medium 105 at an angle of 45° in a Z direction. More specifically, the optical sensor 201 includes an optical system that detects what is called a diffused reflection component of light reflected from the print medium 105.

The second LED 302 is a light source having an irradiation angle of 60° in the Z direction with respect to the surface (measured surface) of the print medium 105. The first photodiode 304 receives light projected from the second LED 302 and reflected from the print medium 105 at an angle of 60° in the Z direction. More specifically, with the angle of light emission and the angle of light reception equal to each other, the optical sensor 201 is configured to have an optical system that detects what is called a specular reflection component of light reflected from the print medium 105.

The third LED 303 is a light source having an irradiation angle of the normal line (90°) with respect to the surface (measured surface) of the print medium 105. The second photodiode 305 and the third photodiode 306 receive light projected from the third LED 303 and reflected from the print medium 105. The amount of light received by the second photodiode 305 and the amount of light received by the third photodiode 306 are different from each other depending on a distance between the optical sensor 201 and the print medium 105, whereby the second photodiode 305 and the third photodiode 306 serve as range sensors that measure the distance between the optical sensor 201 and the print medium 105. Since the distance between the optical sensor 201 and the platen 106 is predetermined, the "paper thickness" of the print medium 105 can be acquired by measuring the distance between the optical sensor 201 and the print medium 105.

While the optical sensor 201 is mounted on the carriage 101 in the present exemplary embodiment, a different configuration may be employed. For example, an optical sensor may be fixed on a printing apparatus. Yet alternatively, an optical sensor may be provided as a measurement device separately from a printing apparatus. The measurement device measures characteristic values of diffused reflection, specular reflection, and the like of a print medium, and transmits characteristic values measured by the measurement device to the printing apparatus, <Block Diagram>

Figure 4:
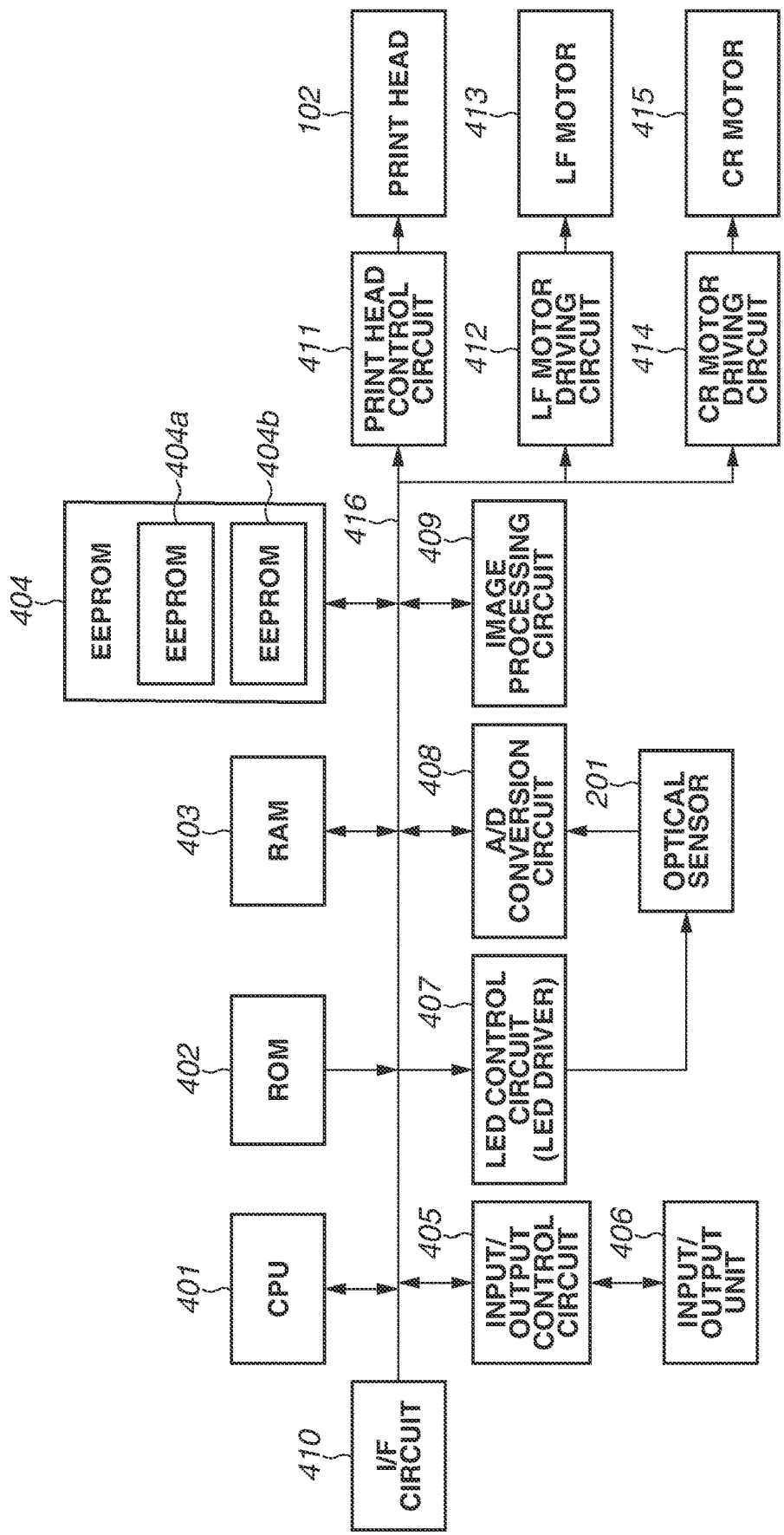
FIG. 4 is a diagram illustrating the block configuration of a control system in the printing apparatus according to the first exemplary embodiment.

FIG. 4 is a diagram illustrating a block configuration of a control system of the printing apparatus 100. A read-only memory (ROM) 402 is a non-volatile memory and stores therein a control program for controlling the printing apparatus 100 and a computer program for implementing operation according to the present exemplary embodiment, for example. The operation according to the present exemplary embodiment is implemented, for example, by a central processing unit (CPU) 401 reading out the computer program onto a random access memory (RAM) 403 and executing a computer program stored in the ROM 402. The PAM 403 is used also as a working memory for the CPU 401. Electrically erasable programmable read-only memory (EEPROM) 404 stores therein data that needs to be kept after the printing apparatus 100 is powered off. The EEPROM 404 includes EEPROM 404*a* and EEPROM 404*h*. Using the CPU 401 and ROM 402, at least functions of the information processing apparatus for performing the print medium determination processing described below are implemented. In the present exemplary embodiment, the EEPROM 404*a* stores therein history of types of print media that have been fed. Information stored therein is handled as history information. The EEPROM 404*b* stores therein preset characteristic values for various print media types and categories of various print media. The categories broadly classified into types of print media that are five categories in the present exemplary embodiment, namely, glossy paper, plain paper, coated paper, film sheet, and special paper. For example, a print medium that is standard glossy paper is classified into the glossy paper category, and a print medium that is premium plain paper is classified into the plain paper category. While print media include those that are not paper medium, the term "sheet" is used in notification to a user in the present exemplary embodiment. The history information and characteristic values for various print media may be stored in a host computer or a server instead of a storage medium in a printing apparatus.

An I/F (interface) circuit 410 connects the printing apparatus 100 to an external network, such as a local area network (LAN). The printing apparatus 100 transmits and receives various jobs and various kinds of data via the I/F circuit 410 to and from an external apparatus, such as a host computer.

The input/output unit 406 includes an input unit and an output unit. The input unit receives a power-on instruction, a print execution instruction, and instructions about settings for the various functions from a user. The output unit displays various kinds of apparatus information such as a power saving mode and also displays screens about settings for the various functions that can be executed by the printing apparatus 100. In the present exemplary embodiment, the input/output unit 406 is an operation panel on the printing apparatus 100, and the input/output unit 406 is connected to a system bus 416 via an input/output control circuit 405 to transmit and receive data from and to the system bus 416. In the present exemplary embodiment, the CPU 401 controls information notification from the output unit.

The input unit may be a keyboard of an external host computer, and may receive user instructions from the external host computer. The output unit may be an LED display device, a liquid crystal display (LCD) display device, or a display device connected to a host apparatus. In a case where the input/output unit 406 is a touch panel, user instructions using software keys can be received. The input/output unit 406 may also be a speaker and a microphone and receive speech input from a user and provide audio output to a user.

An information processing apparatus that includes a CPU and a ROM that have the same functions as the CPU 401 and ROM 402 and is externally connected to the printing apparatus 100 may perform the print medium determination processing described below to determine a print media type to be used in the printing apparatus 100.

When the optical sensor 201 performs the measurement, the CPU 401 controls driving of an LED control circuit 407 to turn on a predetermined LED in the optical sensor 201. Each of the photodiodes 304 to 306 in the optical sensor 201 outputs signals based on received light. The signals are converted into digital signals by the analog-digital (A/D) conversion circuit 408 and are temporarily stored in the RAM 403. Data that is stored after power-off of the printing apparatus 100 is stored in the EEPROM 404b.

A print head control circuit 411 supplies drive signals according to print data to a nozzle driving circuit mounted on the print head 102 and including a selector and a switch, whereby the printing operation of the print head 102 such as a drive sequence of nozzles is controlled. For example, when data to be printed is transmitted from the outside to the I/F circuit 410, the data to be printed is temporarily stored in the RAM 403. The print head control circuit 411 then drives the print head 102 based on print data to be used for printing into which the data to be printed is converted. In the processing, a line feed (LF) motor driving circuit 412 drives a LF motor 413 based on the bandwidth of the print data and the like, whereby the conveyance rollers coupled to the LF motor 413 rotates and consequently conveys a print medium. A carriage (CR) motor driving circuit 414 drives a CR motor 415, whereby the carriage 101 performs scanning via the conveyance belt 103.

Data transmitted from the I/F circuit 410 includes data to be printed and also data on specific settings set in a printer driver. The data to be printed may be stored in a storage unit after reception from the outside via the I/F circuit 410 or may have been stored in advance in a storage unit, such as a hard disk. The CPU 401 controls an image processing circuit 409 to read image data from a storage unit and convert (binarize) the image data into print data for the print head 102. The image processing circuit 409 executes binarization of the image data and also various kinds of image processing, such as color space conversion, horizontal-to-vertical (HV) conversion, gamma correction, and image rotation.

<Overall Flow>

Figure 5:
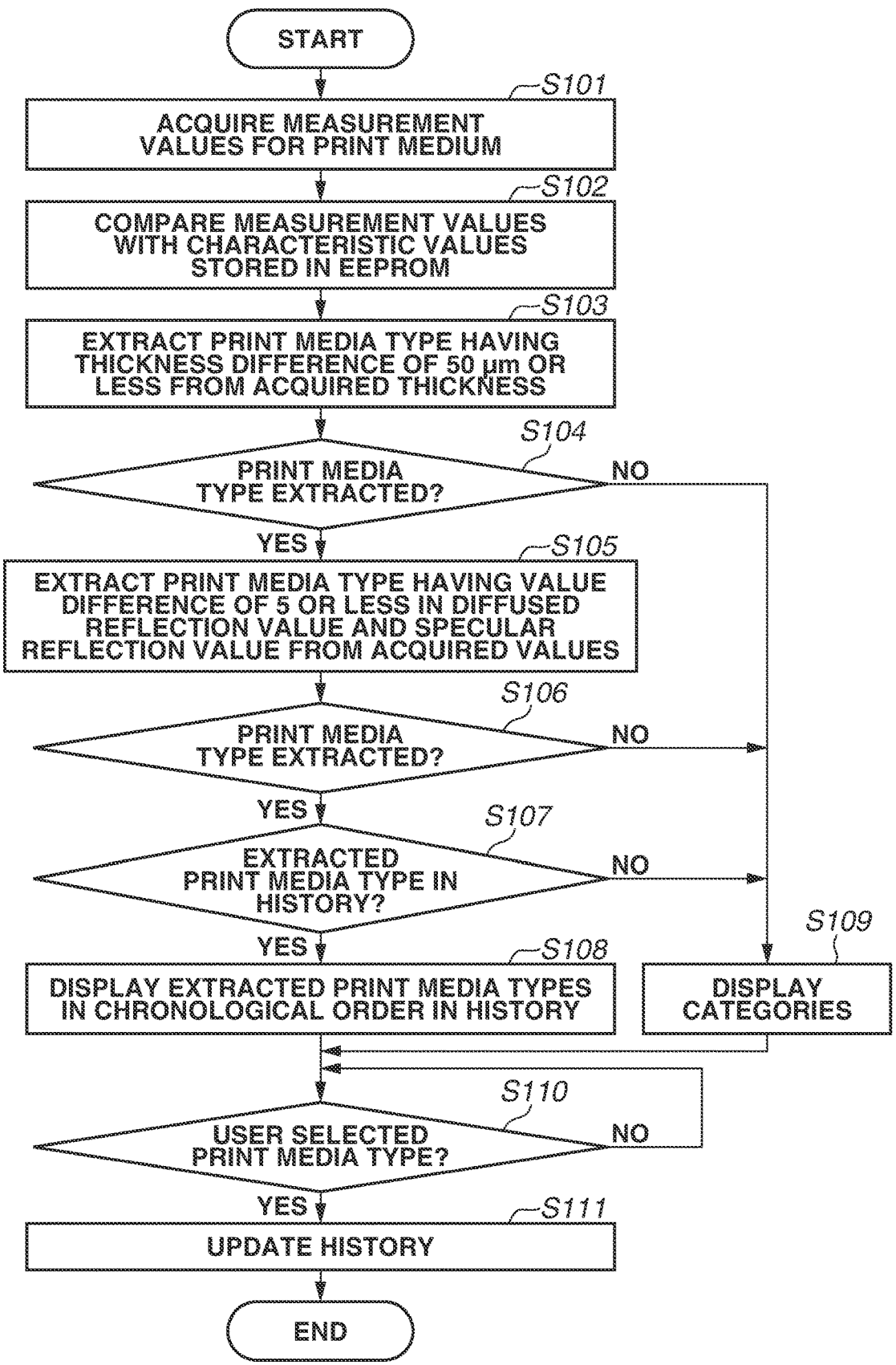
FIG. 5 is a flowchart illustrating print medium determination processing according to the first exemplary embodiment.

FIG. 5 is a flowchart illustrating the print medium determination processing. In the print medium determination processing, characteristics of the print medium 105 on which printing is to be performed are measured to obtain measurement results, the input/output unit 406 is notified of candidates for a print media type based on print media type history information to determine a print media type. Based on a determined print media type, parameters such as the maximum ink usage, the heights of the print heads, the suction force to be applied to a print medium on platen 106, and the degree of correction to the conveyance amount of a print medium are set. Any other control parameters that have effects on characteristics of the print medium may also be used. Processing in steps S101 to S111 in FIG. 5 is implemented, for example, by the CPU 401 illustrated in FIG. 4 reading out the computer program onto the RAM 403 and executing a computer program stored in the ROM 402. Alternatively, the print medium determination processing may be executed using software on a host apparatus. In the present exemplary embodiment, since the input/output unit 406 serves as an operation panel disposed on the printing apparatus 100, notification of candidates for a print media type is provided by displaying names of print media types on the operation panel. The input/output unit 406 may be a display device connected to a host apparatus and the host apparatus. Alternatively, in a case where the input/output unit 406 is a speaker capable of receiving speech input and providing audio output using a microphone function, candidates for a print media type is notified via the speaker, and selection of a print media type is performed by a user voice input inputting a name of a print media type or a corresponding reference numeral to a microphone.

The CPU 401 starts feeding the print medium 105 upon receiving a user instruction to start feeding a sheet via the operation panel included in the input/output unit 406. FIG. 6A is an example of display on the operation panel for receiving input of the instruction to start feeding a sheet. The operation panel includes a display device, two buttons to be operated by the user to move a selecting item up and down, and a select button with which the user can determine the selection.

After start of sheet feeding, the print medium 105 is conveyed by the conveyance rollers to a position on the platen 106 where the optical sensor 201 can perform detection. In step S101, the carriage 101 moves over the print medium 105 in the X direction to acquire a diffused reflection value, a specular reflection value, and a value for the thickness (hereinafter, paper thickness) of the print medium 105 ( ) as measurement values for characteristics of the print medium 105. A diffused reflection value corresponds to the whiteness of a print medium, a specular reflection value corresponds to the glossiness of a print medium. As a characteristic of a print medium, the width of the print medium in the X direction may be used to perform the print medium determination processing. The characteristics measurement of a print medium may be performed at one position on the print medium or may be performed at a plurality of positions to have an average of measurement results. The characteristics measurement may be performed while the optical sensor 201 is stopped or may be performed while the optical sensor 201 moves. Measurement values are temporarily stored in a memory, such as the RAM 403.

In step S102, the CPU 401 then reads out the acquired measurement values from the memory and compares the measurement values with the characteristic values of the various print media types that are previously determined and stored in the EEPROM 404b. In this processing, a print media type that has characteristics corresponding to characteristics indicated by the measurement values is extracted. Details are as described below. FIG. 7A is a table illustrating characteristic values of various print media types that have been stored in the EEPROM 404b. A diffused reflection value and a specular reflection value are values obtained by A/D 10-bit conversion performed on output voltage from the optical sensor 201 receiving light. In step S103, the CPU 401 extracts a print media type having a paper thicknesses difference of 50 μm or less from the acquired paper thickness from among the print media types stored in the EEPROM 404b.

In step S104, the CPU 401 then determines whether a print media type is extracted.

In a case where no print media type is extracted (NO in step S104), which means that there is no applicable print media type, the processing proceeds to step S109. In step S109, all of the categories are displayed on the operation panel as illustrated in FIG. 6B. The categories are displayed in predetermined order. In a case where input of a category selected by the user is received in the display of the categories, print media types that belong to the selected category are displayed as illustrated in FIG. 6C. Input of a print media type selected from among the displayed print media types is then received. In FIG. 6B, an item "ALL" is displayed in the lowest part under the categories of print media types. Upon selection of the item "ALL", all of the print media types are displayed in predetermined order. The print media types may be displayed in chronological order with the one used latest listed on the top.

In a case where there is a print medium extracted in step S104 (YES in step S104), the processing proceeds to step S105. In step S105, the CPU 401 extracts a print media type having a value difference of 5 or less from the acquired diffused reflection value and the acquired specular reflection value from among the print media types stored in the EEPROM 404b. In step S106, the CPU 401 determines whether a print media type is extracted. In a case where no print media type is extracted (NO in step S106), the processing proceeds to step S109. In step S109, the categories are displayed on the operation panel as illustrated in FIG. 6B.

In a case where a print medium is extracted in step S106 (YES in step S106), the processing proceeds to step S107. In step S107, the CPU 401 determines whether there is a usage history for the extracted print media type based on the history information stored in the EEPROM 404a. As illustrated in FIG. 8A, the EEPROM 404a stores therein the history information in association with information indicating how recently each of the print media types has been used in the printing apparatus 100. For the print media type that has been used a plurality of times, information on the last usage is stored in the history, FIGS. 8A to 8C indicate that the print media type that has been used more recently has a smaller number in the "ORDER IN HISTORY" field.

In step S107, in a case where the CPU 401 determines that there is no usage history for the extracted print media type (NO in step S107), the processing proceeds to step S109. In step S109, the CPU 401 displays the categories as illustrated in FIG. 6C. Alternatively, in a case where there is no usage history for the extracted print media type (NO in step S107), the extracted print media types may be displayed in order of addresses in which the print media types are stored in the EEPROM 404b. In a case where the CPU 401 determines that there is a usage history for the extracted print media type (YES in step S107), the processing proceeds to step S108. In step S108, the CPU 401 displays the extracted print media types in a sheet ranking in which the print media type that has been extracted a plurality of times is treated as one type, as illustrated FIG. 6D. In FIG. 6D, the CPU 401 assigns higher priority to the print media type used more recently, and displays names of the print media types in higher priority order from top of the list. With a name of "SHEET RANKING", the user can easily recognize that the names of print media types are displayed in order of precedence of selection, that is, in order of priority. In the present exemplary embodiment, while three print media types having higher priority can be displayed in "SHEET RANKING", FIG. 6D illustrates an example in which only two print media types are displayed since the history information contains two types of the extracted print media types. In the third field from the top, a message "NO SELECTION HISTORY AVAILABLE" is displayed in faint color to be less noticeable than the two print media types, whereby the user is notified that the history information does not contain the third candidate. For example, when the background color on the operation panel is black, the two print media types are displayed in white while the message "NO SELECTION HISTORY AVAILABLE" is displayed in gray having lower brightness than white. Below the message "NO SELECTION HISTORY AVAILABLE", the sheet categories are displayed. When a print media type desired by the user is not found among the print media types displayed on the input/output unit 406, the user can select a print medium of another print media type. FIGS. 9A to 9D illustrate a method for displaying candidates for a print media type in another form of the input/output unit 406. As illustrated in FIG. 9A, candidates at lower rankings may be displayed by a scrolling operation when there is a candidate for a print media type that cannot be displayed on the operation panel at one time. The candidates may be displayed not in order of ranking in a case where the user can recognize the order of priority among the candidates. The order of priority may be represented by displaying the name of the print media type having the highest priority at the center of the operation panel or, as illustrated in FIG. 9B, by using relatively large and bold characters for displaying the names of print media types having higher priority. Furthermore, as illustrated in FIG. 9C, the input/output unit 406 may be a touch panel on which selection can be performed by a touch operation without buttons for moving a cursor. In FIG. 9C, the candidates are displayed with reference numerals 1 to 3 assigned to print media types to indicate the respective rankings. In the example in FIG. 9C, the standard semi-glossy paper with a number 1 is ranked highest. The reference numerals are used for user's recognition of the ranking, and therefore any sign or mark can be used instead of the reference numerals. Additionally, while the categories are displayed below an indication "SHEET CATEGORY", the categories may be displayed without the indication "SHEET CATEGORY". Instead of the categories, print media types may be displayed in chronological order below the candidates for the print media type.

Alternatively, as illustrated in FIG. 9D, only the print media type having the highest priority may be displayed. FIG. 9D is an example in which the candidate is displayed on a touch panel. On the display, "SELECT" is selected to determine the displayed print media type as the type of the print medium 105. In the example in FIG. 9D, the user can select an item indicating "STANDARD SEMI-GLOSSY PAPER" when selecting another print media type that has been extracted and found in the history. After the selection, the display is shifted to the display illustrated in FIG. 9C, on which another print media type can be selected.

In step S110, in a case where the user has selected a print media type using the input/output unit 406 (YES in step S110), the processing proceeds to step S111. In step S1.11, the CPU 401 updates the chronological order in the history stored in the EEPROM 404a based on the print media type selected in step S110. The print medium determination processing ends upon completion of step S110.

Upon completion of preparation for printing after completion of the print medium determination processing, the CPU 401 shifts to a waiting state to receive a printing job from the user. The CPU 401 then starts printing upon receiving a printing job. The updating of the chronological order in the history in step S111 may be performed when a printing job is transmitted from a host computer. The CPU 401 may not to update the history information stored in the EEPROM 404a when a print media type selected and input by the user using the input/output unit 406 is different from a print media type in the job transmitted from the host computer to the printing apparatus 100.

In the print medium determination processing in FIG. 5, a print media type having an applicable paper thickness is extracted in step S103, and a print media type having an applicable diffused reflection value and an applicable specular reflection value is extracted in step S105. The extraction sequence is not limited to this example, and a print media type having an applicable diffused reflection value may be extracted in the first place, for example.

In a case where the optical sensor 201 is included in a measurement device provided separately from the printing apparatus, the characteristic values of a print medium set on the measurement device are acquired by the measurement device and transmitted to the printing apparatus 100. The CPU 401 in the printing apparatus 100 may extract a print media type based on the transmitted characteristic values and notify the input/output unit 406 of a candidate.

The print medium determination processing is described below using a specific example. When the characteristics of the print medium 105 acquired in step S101 are (diffused reflection value, specular reflection value, paper thickness) =(103, 98, 190), a range of paper thicknesses of print media types to be extracted is 140 to 230 μm as illustrated in FIG. 7B. In step S103, the standard glossy paper, the standard semi-glossy paper, and the premium glossy paper, which have paper thicknesses in the range of 140 to 230 μm, are extracted. Since at least one print media type is extracted, the determination in step S104 results in YES, whereby the processing proceeds to step S105.

Ranges of diffused reflection values and specular reflection values of print media types to be extracted in step S105 are 98 to 108 and 95 to 103, respectively. From among the three print media types extracted in step S103, the standard glossy paper and the standard semi-glossy paper, which have characteristic values within these ranges are extracted.

When the chronological order in the history in the history information stored in the EEPROM 404a is as illustrated in FIG. 8A, the standard semi-glossy paper is used more recently out of the two extracted print media types. Accordingly, the standard semi-glossy paper is displayed at the top, followed by the standard glossy paper, on the input/output unit 406 as illustrated in FIG. 6D. When the standard glossy paper is selected by the user, the chronological order in the history is updated as illustrated in FIG. 8B.

For example, when the characteristics of the print medium 105 acquired in step S101 are (diffused reflection value, specular reflection value, paper thickness)=(88, 150, 90), a range of paper thicknesses of print media types to be extracted is 40 to 130 μm as illustrated in FIG. 7C. In step S103, the standard plain paper and the premium plain paper, which have paper thicknesses in the range of 40 to 130 μm, are extracted. Since at least one print media type is extracted, the determination in step S104 results in YES, whereby the processing proceeds to step S105.

Ranges of diffused reflection values and specular reflection values of print media types to be extracted in step S105 are 83 to 93 and 145 to 155, respectively. Neither of the three print media types extracted in step S103 is not a print media type having characteristic values in these ranges. The processing therefore proceeds to step S109, the categories are displayed on the input/output unit 406 as illustrated in FIG. 6B.

As described above, characteristic values of a print medium that has been fed are acquired, and a print media type used more recently are displayed with a higher rank among the candidates for a print media type. With the configuration, the user can be notified of a print media type more likely to be used by the user in a prioritized manner and whereby a workload of the user for selecting a print media type desired by the user can be reduced.

In the above exemplary embodiment, the chronological order of the print media types recently used is stored as the history information. However, the history information is not limited to this example. As the history information, the number of times of each of the print media types having been used may be stored. In the print medium determination processing, when print media types are extracted, the user is notified of the names of the print media types in descending order of the numbers of times of the print media types having been used.

In the first exemplary embodiment, the user is notified of the names of print media types stored in the history information among the print media types extracted in step S105 that are in the history information. In a second exemplary embodiment, a print media type that is not in the history information is also notified by the input/output unit 406 if the print medium has been extracted. In the below description, the same parts as those in the first exemplary embodiment is omitted.

Figure 10:
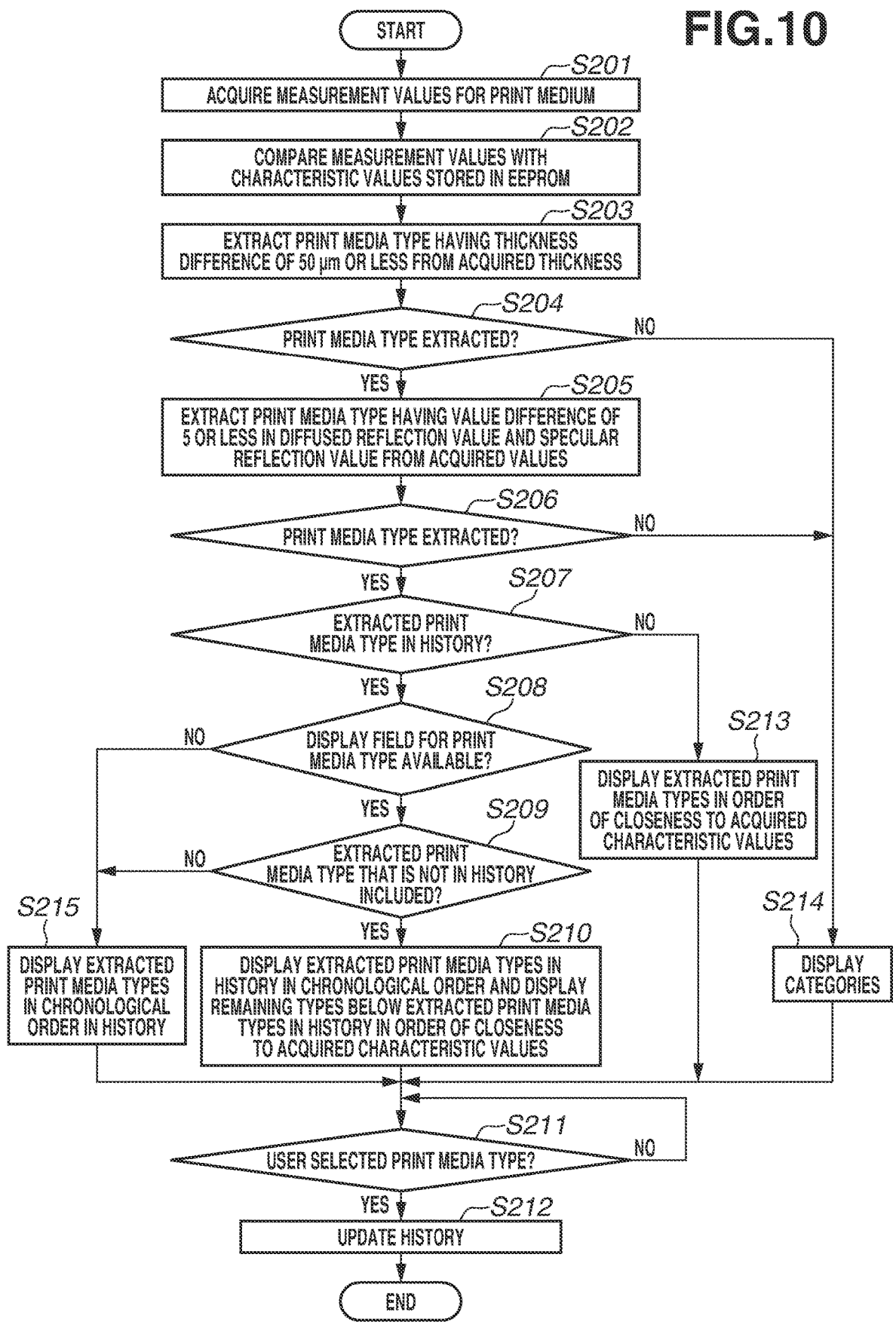
FIG. 10 is a flowchart illustrating print medium determination processing according to the second exemplary embodiment.

FIG. 10 is a flowchart illustrating print medium determination processing according to the second exemplary embodiment. In steps S201 to S206, S211, and S212, the same processing as that in S101 to S106, S110, and S111 in FIG. 5 in the first exemplary embodiment is performed.

In step S201, the CPU 401 acquires the diffused reflection value, the specular reflection value, and the paper thickness of the print medium 105 using the optical sensor 201. In step S202, the CPU 401 then reads out the acquired measurement values from the memory and compares these measurement values with the characteristic values of the print media types that have been previously determined and stored in the EEPROM 404b. The CPU 401 then extracts a print media type having characteristics corresponding to characteristics indicated by the acquired measurement values. In step S203, the CPU 401 extracts a print media type stored in the EEPROM 404b having a paper thickness difference of 50 μm or less from the acquired paper thickness. In step S204, the CPU 401 determines whether any print media type is extracted. In a case where no print media type is extracted (NO in step S204), which means that no print media type has been determined to be applicable, the processing proceeds to step S214. In step S214, the categories are displayed on the operation panel as illustrated in FIG. 6B.

In a case where any print media type is extracted in step S204 (YES in step S204), the processing proceeds to step S205. In step S205, the CPU 401 extracts a print media type stored in the EEPROM 404b having a value difference of 5 or less in the diffused reflection value and the specular reflection value from the acquired diffused reflection value and specular reflection value. In step S206, the CPU 401 then determines whether any print media type is extracted.

In a case where no print media type is extracted (NO in step S206), the processing proceeds to step S214. In step S214, the categories are displayed on the operation panel as illustrated in FIG. 6B.

In a case where a print media type is extracted in step S206 (YES in step S206), the processing proceeds to step S207, in step S207, the CPU 401 determines whether the history information stored in the EEPROM 404a contains the extracted print media type. As illustrated in FIG. 8C, the EEPROM 404a has the history information in association with information indicating how recently each of the print media types has been used in the printing apparatus 100. For the print media type that has been used a plurality of times, the information on the latest usage is stored. In the history. In the case illustrated in FIG. 8C, three print media types have been used and stored as the history information in the EEPROM 404a.

In a case where none of the extracted print media types are in the history information in step S207 (NO in step S207), the processing proceeds to step S213. In step S213, the CPU 401 displays the extracted print media types in order of determination of how close the characteristic values of each of the extracted print media types are to the characteristic values of the print medium 105 that have been acquired in step S201.

In a case where the extracted print media type is in the history information in step S207 (YES in step S207), the processing proceeds to step S208. In step S208, the CPU 401 determines whether any field in which a print media type is to be displayed is still available if the names of the extracted print media types that are in the history information are displayed on the operation panel, in a case where a field is not available (NO in step S208), the processing proceeds to step S215. In step S215, the CPU 401 displays the names of all of the extracted print media types that are in the history information on the operation panel in chronological order in the history.

In a case where a field is available (YES in step S208), the processing proceeds to step S209. In step S209, the CPU 401 determines whether the print media types extracted in step S205 include a print media type that is not in the history information. In a case where the extracted print media types do not include a print media type that is not in the history information (NO in step S209), the processing proceeds to step S215. In step S215, the CPU 401 displays the names of the extracted print media types that are in the history information on the operation panel in chronological order in the history. In a case where the extracted print media types include a print media type that is not in the history information (YES in step S209), the processing proceeds to step S210. In step S210, the CPU 401 displays the names of the extracted print media types that are in the history information in chronological order in the history from the top of the list. Further, below the names of the extracted print media types that are in the history information, the CPU 401 displays the names of the extracted print media types that are not in the history information in order of determination of how close the characteristic values of each of the print media types are to the characteristic values of the print medium 105 that have been acquired in step S201.

In step S211, in a case where user selection of a print media type is received via the operation panel which is the input/output unit 406 (YES in step S211), the selection is input to the CPU 401. In step S212, the CPU 401 updates the chronological order in the history stored in the EEPROM 404a based on the print media type selected in step S211. The print medium determination ends upon completion of step S212.

Description using a specific example is given below. In the example, the characteristics of the print medium 105 acquired in step S201 have the same values as those in the example described in the first exemplary embodiment, which are (diffused reflection value, specular reflection value, paper thickness)=(103, 98, 190) when the EEPROM 404a has the history information as illustrated in FIG. 8C. In steps S201 to S206, the same processing as that in steps S101 to S106 in the first exemplary embodiment is performed. Accordingly, the print media types extracted in the processing in step S205 are the standard glossy paper and the standard semi-glossy paper, which means that there is at least one print media type extracted, and the processing proceeds to step S207. Information indicating the standard semi-glossy paper is found in the history information illustrated in FIG. 8C in step S207 (YES in step S207), and a field in which a print media type is to be displayed is still available because only one print media type has been determined to be displayed while up to three print media types can be displayed (YES in step S208). The processing therefore proceeds to step S210 since there is a print media type that is not in the history information but has been extracted. In step S210, as illustrated in FIG. 6D, the extracted print media types are displayed with the standard semi-glossy paper (a print media type stored in the history information) at the top followed by the standard glossy paper (a print media type that is not in the history information but has been extracted).

With the above described configuration, a print media type not in the history information is also displayed, whereby a workload of the user for selecting a print media type desired by the user can be reduced even when a desired print media type has not been used.

In the first and the second exemplary embodiments, the user is notified of candidates with print media types in the history information ranked higher that have been used. In a third exemplary embodiment, weights are assigned to characteristic values and the history information with respect to each print media type, and the user is notified of candidates with a print media type ranked higher that has a larger weighting index value. Description of the same parts as those in the first and the second exemplary embodiments is omitted.

In the present exemplary embodiment, in addition to the chronological order of usage, information as the history information on how recently each print media type has been used and also information on how long it has passed up to the current execution of print medium determination since the last usage of each print media type are stored in the EEPROM 404a, in association with the corresponding print media type.

When print medium determination processing is executed, weighting index values are assigned to print mediums stored in the EEPROM 404a in accordance with how recently each print media type has been used. In this assignment, a larger weighting index value is assigned to a print media type if a shorter period of time has passed since the last usage. The weighting index values are assigned by the CPU 401 and temporarily stored in the RAM 403.

When the print medium 105 is fed, the optical sensor 201 acquires the characteristic values of the print medium 105. The CPU 401 compares the acquired characteristic values of the print medium 105 with the characteristic values of each of the print media types stored in the EEPROM 404b and extracts print media types that have characteristics corresponding to characteristics indicated by measurement values. A weighting index value that indicates how close the characteristic values of each of the extracted print media types are to the characteristic values of the print medium 105 is assigned to the corresponding print media type and temporarily stored in the RAM 403.

The weighting index values assigned to each of the extracted print media types based on the history information of the extracted print media types and the weighting index values assigned based on the characteristic values are summed, and the user is notified of the extracted print media types using the input/output unit 406 in descending order of the summation results.

Each of the methods discussed in the above-described exemplary embodiments is a method for selecting a print media type in the "user determination mode" that includes notifying at step S108 (FIG. 5) and steps S210, S213, and S215 (FIG. 10) the user via the input/output unit 406 of a plurality of print media types, notifying a user of candidates, and then prompting the user at step S110 (FIG. 5) and step S211 (FIG. 10) to determine a print media type. In a fourth present exemplary embodiment, an "automatic determination mode" is executed. In the "automatic determination mode", if the user does not make a selection within certain period of time after being notified of a plurality of print media types, the print media type ranked the highest is determined to be a selection. Description of the same parts as those in the above-described exemplary embodiments is omitted.

AUTOMATIC DETERMINATION MODE

Figure 12:
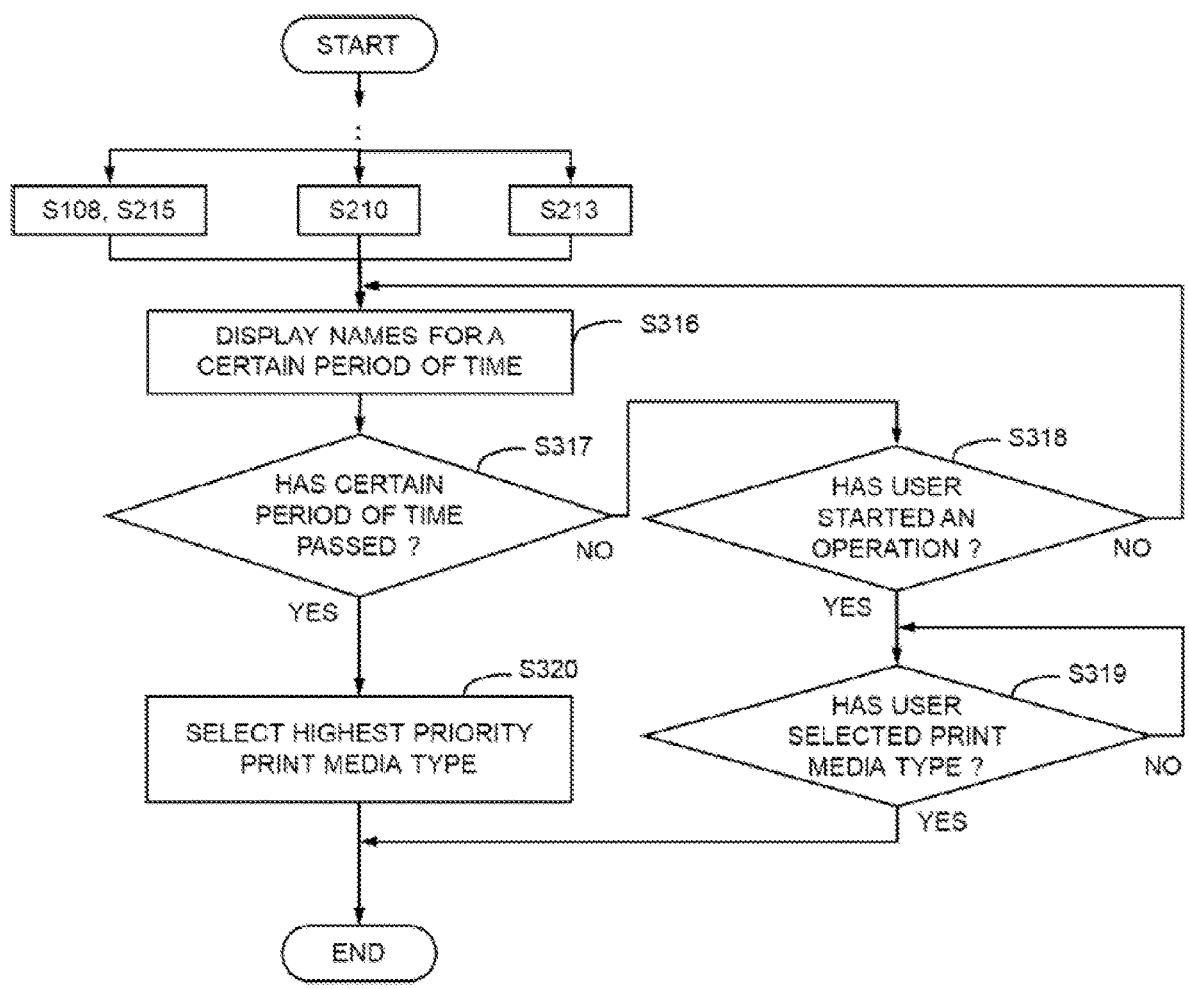

FIG. 12 is a flowchart illustrating a print medium determination processing according to the fourth exemplary embodiment. The same processing as that in steps S101 to S109 in the print medium determination processing in FIG. 5 according to the first exemplary embodiment is performed in the present exemplary embodiment. In the present exemplary embodiment, the names of candidate print media types are displayed on an operation panel that is the input/output unit 406 as illustrated in FIG. 11 in step S108. A display may be from S108 or S109 in FIG. 5 or from steps, S210, S213, S214, or S215 in FIG. 10. The names are displayed at step S316 for a certain period of time While the names are displayed for the certain period of time at step S316, messages that an automatic selection is to be made and that the user can make a manual selection are presented at step S316 at the same time as illustrated in FIG. 11.

It is determined at steps S317 and S318 whether the user has any operation within the certain period of time. That is, it is determined at step S317 whether the certain period of time has passed and, if not (NO at step S317), it is determined at step S318 whether the user starts an operation within the certain period of time. If it is determined at step S318 that the user has not started an operation within the certain period of time (NO at step S318), the names and messages continue to be displayed and the process returns to step S316. If it is determined at step S318 that the user has started an operation within the certain period of time (YES at step S318), the displaying in FIG. 11 is continued at step S319 after the certain period of time and is continued at step S319 (NO at step S319) until the user selects a print medium ("user determination mode") (YES at step S319), at which time the print medium determination is ended. In a case where the categories are displayed as in step S109, the print media type is determined when the user selects a print media type at step S319 as in the case of the first exemplary embodiment.

If it is determined at step S317 that the user does not start any operation within the certain period of time, that is, if it is determined at step S317 that the certain period of time has passed (YES at step S317), a print media type to which the highest priority has been given, which is the standard semi-glossy paper in the example illustrated in FIG. 11, is determined at step S320 ("automatic determination mode") to be the selection, and the print medium determination is ended.

The same processing as that in steps S201 to S210 and S213 to S215 in the print medium determination processing in FIG. 10 according to the second exemplary embodiment may be performed. In a case where the names of a plurality of print media types are displayed on the input/output unit 406 (steps S210, S213, and S215), a print media type ranked highest is determined to be the selection if the user does not start any operation within the certain period of time.

Among the automatic determination mode and the user determination mode, a mode may be selected and set by the user using the input/output unit 406. The automatic determination may be performed when a pri3nt media type having characteristic values that are closest to measurement values is ranked highest, and the automatic determination may be not performed when such a print media type is ranked second highest or lower. With this configuration, the automatic determination is performed when the reliability of detection of a print medium is high, whereby user convenience is enhanced.

As described above, the names of a plurality of print media types are displayed and a print media type ranked highest is selected if the user does not start any operation within the certain period of time, whereby a workload of the user for selecting a print media type can be further reduced.

Other Embodiments

While the printing apparatus according to the above-described exemplary embodiments is an ink jet printing apparatus that discharges ink as a printing agent, an electrophotographic printing apparatus that uses powder toner as a printing agent may be used.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

According to the above described exemplary embodiments, user convenience in print medium determination can be improved.

While the present invention has been described with reference to exemplary, embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 019-016168, filed Jan. 31, 2019, which is hereby incorporated by reference herein in its entirety.

What is claimed is:

1. An information processing apparatus comprising:
one or more memory devices that store a set of instructions; and
one or more processors to execute the set of instructions to perform operations including:
acquiring, as a measurement result, a characteristic of a print medium measured by a sensor and to be used in a printing apparatus,
obtaining information on a stored characteristic of each of a plurality of print media types from a memory, wherein the stored characteristic includes characteristic values of various print media types in the memory,
determining multiple candidates for print media types based on the measurement result and the obtained information on the stored characteristic,
causing, in a case where the determined multiple candidates includes at least one print media type used in the printing apparatus indicated in usage history information, a notification device to provide notification, to a user, of information indicating the determined multiple candidates for print media types as the notified multiple candidates for print media types, and
receiving, after the notification device provides the notification to the user and in a case where one print media type is selected by the user from the notified multiple candidates for print media types, input of information corresponding to the one print media type selected by the user and set to be a print media type to be used in the printing apparatus,
wherein the information indicating the determined multiple candidates for print media types is included in the obtained information on the stored characteristic of each of the plurality of print media types, and
wherein, in a case where an operation is not received from the user within a predetermined period of time after the notification device provides the notification to the user and where a length of the predetermined period of time results in reducing a workload of the user for selecting the one print media type, one of the notified multiple candidates for print media types is set as the print media type to be used in the printing apparatus.

2. The information processing apparatus according to claim 1, wherein the causing includes causing the notification device to provide the notification to the user such that the notification further includes information which indicates that the at least one print media type used in the printing apparatus indicated in the usage history information is presented with a priority higher than a print media type not having the usage history information among the notified multiple candidates for print media types.

3. The information processing apparatus according to claim 1, wherein the causing includes causing the notification device to provide the notification to the user of the at least one print media type used in the printing apparatus indicated in the usage history information in a manner that allows the user to recognize a priority order based on the usage history information among the notified multiple candidates for print media types.

4. The information processing apparatus according to claim 3, wherein, in the priority order, a higher priority is given to a print media type used more recently by the user based on the usage history information.

5. The information processing apparatus according to claim 3, wherein the determining of the multiple candidates for print media types includes determining the priority order based on (i) an index value according to closeness between values of the stored characteristic of each of the plurality of print media types and the acquired characteristic indicated in the measurement result and (ii) an index value assigned to each print media type in the memory based on the usage history information related to a length of time that has passed since a last usage by the user of each print media type to which an index value is assigned.

6. The information processing apparatus according to claim 1, wherein, in a case where an operation is not received from the user within the predetermined period of time after the notification device provides the notification to the user and where the length of the predetermined period of time results in reducing the workload of the user for selecting the one print media type, the determining of the multiple candidates for print media types includes determining that a print media type ranked highest in the notification to the user is set as the print media type to be used in the printing apparatus.

7. The information processing apparatus according to claim 1, wherein, in a case where there is a print media type having a characteristic closest to the acquired characteristic indicated in the measurement result among the plurality of print media types, of which characteristic values are stored in the memory, and ranked highest in order in the usage history information, and the one print media type is not selected by the user, the print media type having the closest characteristic is set as the print media type to be used in the printing apparatus.

8. The information processing apparatus according to claim 1, wherein the usage history information includes information on print media types that have been set for printing by the printing apparatus.

9. The information processing apparatus according to claim 8, wherein the usage history information includes information on print media types that have been input.

10. The information processing apparatus according to claim 8, wherein the usage history information indicates (i) the print media types that have been set for printing by the printing apparatus and (ii) order of closeness in time from when each print media type has been used.

11. The information processing apparatus according to claim 1, wherein the measurement result acquired by the sensor includes at least one of a diffused reflection value of the print medium, a specular reflection value of the print medium, and a thickness value of the print medium.

12. The information processing apparatus according to claim 11, wherein the sensor includes a light-emitting diode and a photodiode, and wherein the measurement result is acquired by the light-emitting diode projecting light and by the photodiode receiving reflected light from the print medium.

13. The information processing apparatus according to claim 1, wherein the causing includes causing the notification device to provide notification of a name of a print media type.

14. The information processing apparatus according to claim 1, further comprising:
a printing mechanism configured to perform printing of an image on the print medium; and
a conveyance unit having a motor and configured to convey the print medium to a position at which printing is performed on the print medium by driving the motor,
wherein the printing mechanism performs the printing of the image on the print medium in a case where the print medium is conveyed by the motor of the conveyance unit to a position at which the printing mechanism is able to perform the printing.

15. The information processing apparatus according to claim 14, further comprising a carriage on which the printing mechanism is mounted and configured to be movable,
wherein the sensor is mounted on the carriage and measures the characteristic of the print medium in a case where the print medium is conveyed by the motor of the conveyance unit to a position at which the sensor is able to measure the characteristic of the conveyed print medium.

16. The information processing apparatus according to claim 1, wherein, in a case where the determining includes determining absence of candidates for print media types, the causing includes causing the notification device to provide notification of information indicating categories broadly classified into print media types that include at least one of the following: glossy paper, plain paper, coated paper, film sheet, and special paper.

17. The information processing apparatus according to claim 2, wherein, the causing includes causing the notification device to provide notification of only the at least one print media type used in the printing apparatus indicated in the usage history information among the multiple candidates for print media types.

18. The information processing apparatus according to claim 1, wherein, in the determining of the multiple candidates for the print media types, the determining is:
(A) first based on one of (i) a thickness value of the print medium acquired in the measurement result, and then (ii) a diffused reflection value and a specular reflection value in the measurement result, and then based on the other of (i) the thickness value of the print medium, and then (ii) the diffused reflection value and the specular reflection value, and then
(B) based on the usage history information by applying the usage history information to a determined result of (A).

19. A method of determining a determined print media type, the method comprising:
acquiring, as a measurement result, a characteristic of a print medium measured by a sensor and to be used in a printing apparatus;
obtaining information on a stored characteristic of each of a plurality of print media types from a memory, wherein the stored characteristic includes characteristic values of various print media types in the memory;
determining multiple candidates for print media types based on the measurement result and the obtained information on the stored characteristic;
providing, in a case where the determined multiple candidates includes at least one print media type used in the printing apparatus indicated in usage history information, notification, to a user, of information indicating the determined multiple candidates for print media types as the notified multiple candidates for print media types; and
receiving, after the notification is provided to the user and in a case where one print media type is selected by the user from the notified multiple candidates for print media types, input of information corresponding to the one print media type selected by the user and set to be a print media type to be used in the printing apparatus,
wherein the information indicating the determined multiple candidates for print media types is included in the obtained information on the stored characteristic of each of the plurality of print media types, and
wherein, in a case where an operation is not received from the user within a predetermined period of time after the notification is provided to the user and where a length of the predetermined period of time results in reducing a workload of the user for selecting the one print media type, one of the notified multiple candidates for print media types is set as the print media type to be used in the printing apparatus.

20. The method according to claim 19, wherein the providing includes providing the notification to the user such that the notification further includes information which indicates that the at least one print media type used in the printing apparatus indicated in the usage history information is presented with a priority higher than a print media type not having the usage history information among the notified multiple candidates for print media types.

21. The method according to claim 19, wherein the providing includes providing the notification to the user of the at least one print media type used in the printing apparatus indicated in the usage history information in a manner that allows the user to recognize a priority order based on the usage history information among the notified multiple candidates for print media types.

22. The method according to claim 21, wherein, in the priority order, a higher priority is given to a print media type used more recently by the user based on the usage history information.

23. The method according to claim 19, further comprising setting a parameter to be used for printing in the printing apparatus, based on the one print media type indicated in the received input information.

24. The method according to claim 19, wherein, in a case where an operation is not received from the user within the predetermined period of time after the notification is provided to the user and where the length of the predetermined period of time results in reducing the workload of the user for selecting the one print media type, a print media type ranked highest in the notification to the user is set as the print media type to be used in the printing apparatus.

25. The method according to claim 19, wherein the usage history information includes information on print media types that have been set for printing by the printing apparatus.

26. A non-transitory computer-readable storage medium storing a program to cause a computer to perform a method of determining a determined print media type, the method comprising:
acquiring, as a measurement result, a characteristic of a print medium to be used in a printing apparatus;
providing notification of information indicating a print media type;
obtaining information on a stored characteristic of each of a plurality of print media types from a memory;

providing, to a user and based on (i) the measurement result, (ii) the obtained information on the stored characteristic, and (iii) usage history information indicating at least one print media type used by the user in the printing apparatus, notification of information indicating multiple candidates for print media types for which the obtained information on the stored characteristic corresponds to a characteristic indicated in the measurement result and which has a usage history indicated in the usage history information; and receiving from the user, after providing the notification of the information indicating the multiple candidates for print media types and the usage history information to the user, input of information corresponding to one print media type in the multiple candidates for print media types set to be a print media type to be used in the printing apparatus, wherein the notification provided further includes information indicating that the determined multiple candidates is included in the obtained information on the stored characteristic of each of the plurality of print media types, and wherein, in a case where an operation is not received from the user within a predetermined period of time after providing the notification to the user and where a length of the predetermined period of time results in reducing a workload of the user for selecting a print media type, a print media type notified is set as the print media type to be used in the printing apparatus.

27. A method for an information processing apparatus, the method comprising:

acquiring, as a measurement result, a characteristic of a print medium measured by a sensor and to be used in a printing apparatus;

obtaining information on a stored characteristic of each of a plurality of print media types from a memory, wherein the stored characteristic includes characteristic values of various print media types in the memory;

determining multiple candidates for print media types based on the measurement result and the obtained information on the stored characteristic;

causing, in a case where the determined multiple candidates includes at least one print media type used in the printing apparatus indicated in usage history information, a notification device to provide notification, to a user, of information indicating the determined multiple candidates for print media types as the notified multiple candidates for print media types; and receiving, after the notification device provides the notification to the user and in a case where one print media type is selected by the user from the notified multiple candidates for print media types, input of information corresponding to the one print media type selected by the user and set to be a print media type to be used in the printing apparatus, wherein the information indicating the determined multiple candidates for print media types is included in the obtained information on the stored characteristic of each of the plurality of print media types, and wherein, in a case where an operation is not received from the user within a predetermined period of time after the notification device provides the notification to the user and where a length of the predetermined period of time results in reducing a workload of the user for selecting the one print media type, one of the notified multiple candidates for print media types is set as the print media type to be used in the printing apparatus.

* * * * *